(12) United States Patent
Marume (10) Patent No.: US 6,289,075 B1
(45) Date of Patent: Sep. 11, 2001

(54) X-RAY CT APPARATUS

(75) Inventor: Takashi Marume, Otsu (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 09/427,013

(22) Filed: Oct. 25, 1999

(30) Foreign Application Priority Data

Oct. 28, 1998 (JP) .................................................. 10-306685

(51) Int. Cl.[7] .................................................... A61B 6/00
(52) U.S. Cl. ................................................. 378/8; 378/16
(58) Field of Search ................... 378/8, 21, 16, 378/19, 20

(56) References Cited

U.S. PATENT DOCUMENTS

| | | | |
|---|---|---|---|
| 5,379,333 | * | 1/1995 | Toth ........................................ 378/16 |
| 5,459,769 | * | 10/1995 | Brown ...................................... 378/8 |
| 5,612,985 | * | 3/1997 | Toki et al. ............................... 378/4 |

* cited by examiner

Primary Examiner—Robert H. Kim
Assistant Examiner—Irakli Kiknadze
(74) Attorney, Agent, or Firm—Arent Fox Kintner Plotkin & Kahn, PLLC

(57) ABSTRACT

This invention provides an X-ray CT apparatus for performing a pre-CT which is a form of computerized tomography carried out with low doses beforehand in order to determine timing of starting a production CT which is a form of computerized tomography for acquiring images for use in diagnosis. As a radiographic mode of the pre-CT executed for a monitoring purpose, a radiographic mode suited to the purpose is selected from among three radiographic modes, i.e. a continuous radiographic mode, an intermittent radiographic mode and a combined intermittent and continuous radiographic mode. The apparatus may set, as necessary, a delay time lasting from a point of time when a pre-CT starting instruction is given to a point of time for starting the pre-CT. A coloring state of a contrast medium in a region of concern may be determined accurately at all times by executing the pre-CT. The pre-CT is started, and a switch from intermittent radiography to continuous radiography is carried out, always at appropriate times. Thus, the timing of starting the production CT may be determined properly at all times.

8 Claims, 6 Drawing Sheets

X-RAY CT APPARATUS

BACKGROUND OF THE INVENTION

(1) Field of the Invention

This invention relates to X-ray CT apparatus for performing X-ray computerized tomography (X-ray CT) with contrast media injected to patients, in which a CT for acquiring images for a diagnostic purpose (hereinafter called "production CT") is preceded by a pre-CT for a monitoring purpose which is carried out with low doses in order to determine the timing of starting the production CT. More particularly, the invention relates to a technique for carrying out the pre-CT in an appropriate radiographic mode.

(2) Description of the Related Art

Figure 1:
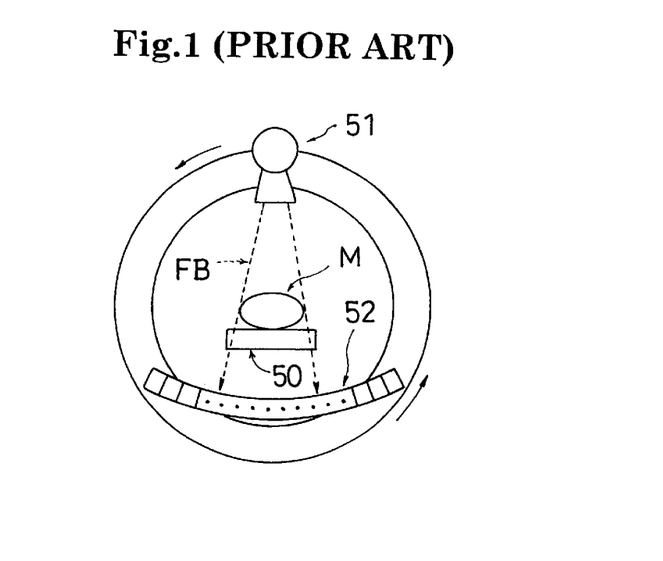
FIG. 1 is a schematic view showing a principal portion of an image pickup system in a conventional X-ray CT apparatus.

An X-ray CT apparatus (X-ray computerized tomographic apparatus) used in a hospital or the like, as shown in FIG. 1, includes an X-ray tube 51 and a multi-channel X-ray detector 52 opposed to each other across a patient M placed on a top board 50. While the X-ray tube 51 and X-ray detector 52 are revolved about the body axis of patient M, a fan beam FB is emitted from the X-ray tube 51. Based on X-ray detection data outputted from the X-ray detector 52, an image reconstruction process is carried out to acquire computed tomographic images (CT images).

The conventional apparatus may be used to perform an X-ray CT of an internal organ (e.g. the liver) of a patient with a contrast medium applied thereto. This is done in order to check presence and position of a tumor by fixation (i.e. coloring) of the contrast medium in a region of concern in the CT images acquired. However, in performing an X-ray CT with a contrast medium, it is necessary to start a radiographic process (production CT) when the contrast medium has fully spread to the region of concern such as the liver.

Thus, the conventional X-ray CT apparatus allows a pre-CT to be carried out with low doses for monitoring purposes before a production CT in order to check whether the contrast medium has spread to the region of concern. The production CT is started after confirming by the CT images acquired from the pre-CT that the contrast medium has fully spread to the region of concern.

Figure 2:
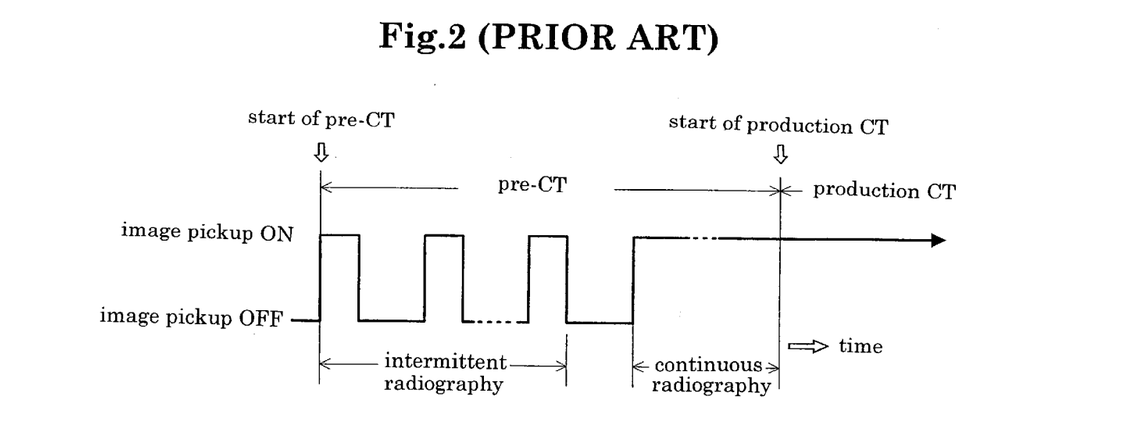
FIG. 2 is a graph showing progress of an X-ray CT by the conventional apparatus.

Further, it is conventional practice to perform the pre-CT in a combination of intermittent and continuous radiographic processes in which an intermittent radiography is executed for a predetermined period, and then a continuous radiography is executed. Specifically, as shown in FIG. 2, spreading conditions of the contrast medium are checked from time to time by observing CT images acquired from the intermittent radiography at an initial stage where the contrast medium has not spread to the full. When the contrast medium is thought to have spread to some extent, spreading conditions of the contrast medium are checked continuously by means of CT images acquired from the continuous radiography. Exposure dose is reduced for the intermittent radiography.

However, the conventional X-ray CT apparatus has a drawback of sometimes failing to determine the timing of starting the production CT correctly. This is because the pre-CT performed in the combination of intermittent and continuous radiographic processes can be ill suited for checking the spreading conditions of the contrast medium. On such an occasion, it is impossible to determine the timing of starting the production CT correctly.

SUMMARY OF THE INVENTION

This invention has been made having regard to the state of the art noted above, and its object is to provide an X-ray CT apparatus which enables the timing of starting a production CT to be determined correctly at all times.

The above object is fulfilled, according to this invention, by an X-ray CT apparatus for performing a pre-CT which is a form of computerized tomography carried out with low doses beforehand in order to determine timing of starting a production CT which is a form of computerized tomography for acquiring images for use in diagnosis, the apparatus comprising:

an X-ray emitting device for emitting X rays toward a patient;

an X-ray detecting device for detecting X rays transmitted through the patient;

a revolving device for revolving the X-ray emitting device and the X-ray detecting device about the patient;

an image reconstructing device for reconstructing sectional images of the patient based on X-ray detection data received from the X-ray detecting device;

a pre-CT control device for controlling the X-ray emitting device according to a radiographic mode of the pre-CT;

a production CT control device for controlling the X-ray emitting device according to radiographic conditions of the production CT; and a pre-CT radiographic mode setting device for selecting and setting, as the radiographic mode of the pre-CT, one of three radiographic modes, i.e. a continuous radiographic mode for performing only a continuous radiography by continuously emitting X rays in low doses, an intermittent radiographic mode for performing only an intermittent radiography by intermittently emitting X rays in low doses, and a combined intermittent and continuous radiographic mode for performing the intermittent radiography and the continuous radiography in combination.

In performing X-ray tomography with the X-ray CT apparatus having the above construction, a contrast medium is given to a patient to be radiographed, and the pre-CT radiographic mode setting device is operated to select and set a radiographic mode for the pre-CT suited to the purpose of radiography, from among the continuous radiographic mode, the intermittent radiographic mode and the combined intermittent and continuous radiographic mode. Subsequently, the pre-CT is executed in the selected radiographic mode with lower doses than for the production CT to acquire sectional images. The operator monitors a coloring state of the contrast medium in a region of concern appearing in the sectional images acquired. When the coloring state of the contrast medium is found appropriate, the pre-CT is stopped and the production CT is started.

Preferably, the X-ray CT apparatus according to this invention further comprises a delay time setting device for setting a delay time lasting from a point of time when a pre-CT starting instruction is given to a point of time for starting the pre-CT.

With the X-ray CT apparatus having the above construction, the pre-CT is deferred for the delay time set by the delay time setting device to last from the point of time when a pre-CT starting instruction is given. Only upon lapse of the delay time, the pre-CT is started. During the delay time for deferring the pre-CT, the operator checks for any leakage of the contrast medium injected.

A point of time for starting a pre-CT in an X-ray CT performed by using a contrast medium must be associated with a point of time for starting a contrast medium injection. Particularly, for a pre-CT in the combined intermittent and continuous radiographic mode, the timing of switching between intermittent radiography and continuous radiography must also be associated with the point of time for starting a contrast medium injection. With the X-ray CT apparatus according to this invention, a pre-CT is always started upon lapse of a selected delay time. Thus, the association between the point of time for starting the pre-CT and the point of time for starting the contrast medium injection is secured, whereby the pre-CT is always started at the right time. The association between the timing of switching from intermittent radiography to continuous radiography and the point of time for starting the contrast medium injection is also secured. Thus, a switch is made between intermittent radiography and continuous radiography always with appropriate timing. As a result, a time for starting a production CT is determined accurately.

Without the above delay time setting function, the pre-CT would be started after a start of contrast medium injection and the operator's checking for any leakage of the contrast medium injected. However, since variations would occur with the checking time, the associations could not be secured between the point of time for starting the pre-CT and the point of time for starting the contrast medium injection, or between the timing of switching between intermittent radiography and continuous radiography and the point of time for starting the contrast medium injection.

Preferably, the X-ray CT apparatus according to this invention further comprises a production CT automatic starting device for automatically starting the production CT upon detection that a measured CT value of a predetermined region of concern in sectional images acquired from the pre-CT has reached a predetermined reference CT value.

With the above construction, the production CT automatic starting device automatically starts the production CT when the measured CT value of a predetermined region of concern in sectional images acquired from the pre-CT are detected to have reached a predetermined reference CT value. Since the measured CT value and the coloring state of the contrast medium are in an excellent corresponding relationship, the measured CT value enables a determination whether the coloring state of the contrast medium in the region of concern is sufficient for starting the production CT.

BRIEF DESCRIPTION OF THE DRAWINGS

For the purpose of illustrating the invention, there are shown in the drawings several forms which are presently preferred, it being understood, however, that the invention is not limited to the precise arrangement and instrumentalities shown.

FIGS. 4A through 4C are graphs showing specific examples of radiographic modes of a pre-CT by the apparatus embodying this invention, in which

DESCRIPTION OF THE PREFERRED EMBODIMENTS

A preferred embodiments of the present invention will be described in detail hereinafter with reference to the drawings.

Figure 3:
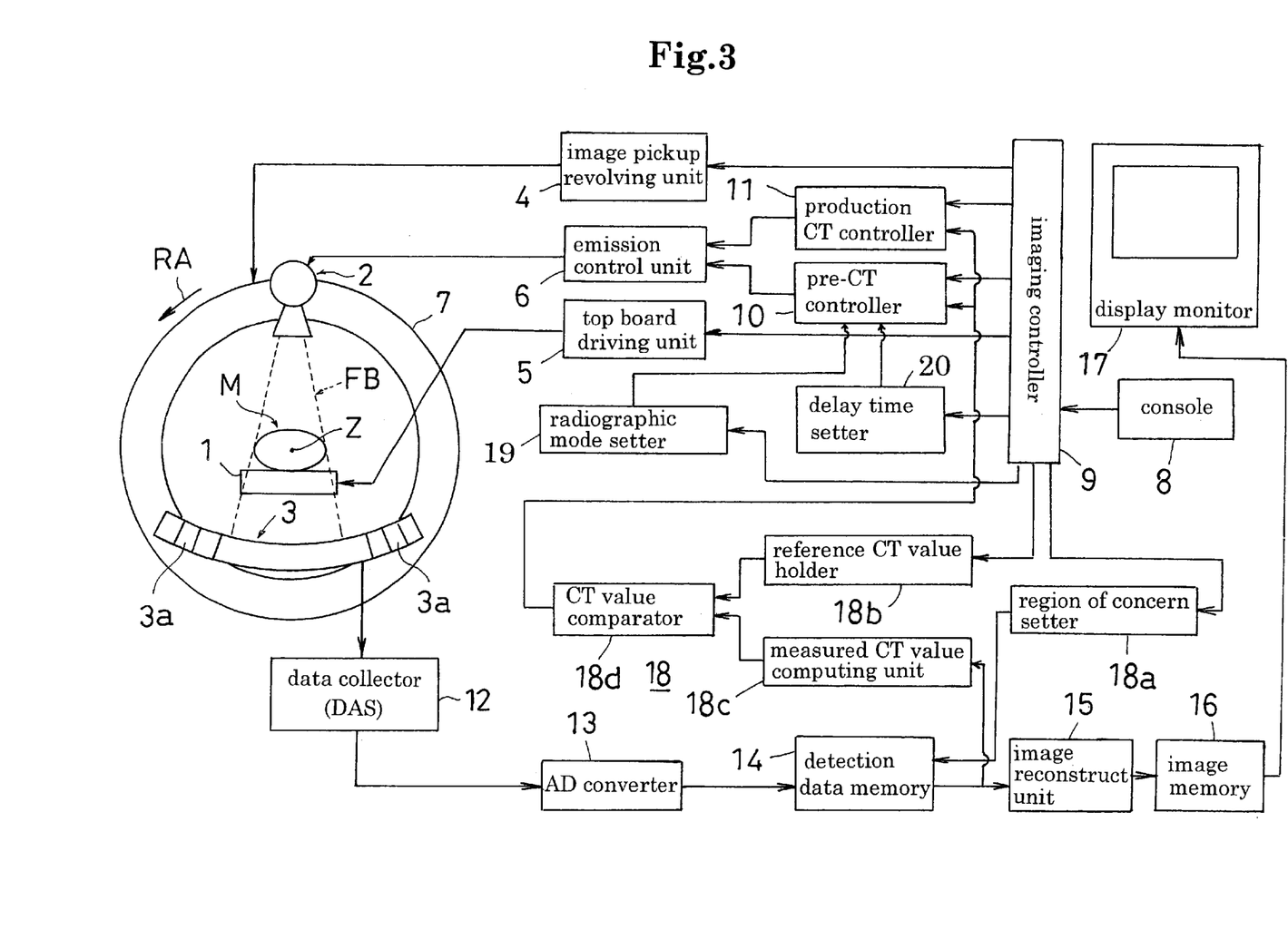
FIG. 3 is a block diagram of an entire X-ray CT apparatus in one embodiment of this invention.

FIG. 3 is a block diagram of an entire X-ray CT apparatus embodying this invention.

As shown in FIG. 3, the X-ray CT apparatus includes a movable top board 1 for supporting a patient M, and an image pickup having an X-ray tube 2 for emitting X rays and an X-ray detector 3 for detecting transmitted X rays. The X-ray tube 2 and X-ray detector 3 are opposed to each other across the patient M. The apparatus further includes an image pickup revolving unit 4 for revolving the X-ray tube 2 and X-ray detector 3, as opposed to each other, about the body axis of patient M in a direction indicated by an arrow RA.

The top board 1 is constructed movable fore and aft (along the body axis Z of the patient) and up and down with the patient M placed thereon. The top board 1 is moved under control of a top board driving unit 5.

The X-ray tube 2, while in revolution, irradiates the patient M with a fan beam FB with selected irradiating conditions such as a tube voltage and a tube current, under control of an emission control unit 6 including a high voltage generator.

The X-ray detector 3 is a multi-channel detector having numerous, e.g. in the order of 1000, X-ray detecting elements $3a$ arranged along an expanse of fan beam FB. The X-ray detector 3 outputs X-ray detection data as the fan beam FB is emitted from the X-ray tube 2 in revolution.

In the image pickup in this embodiment, the X-ray tube 2 and X-ray detector 3 are integrated through a rotary ring 7. Under control of the image pickup revolving unit 4, the rotary ring 7 is rotatable to revolve the X-ray tube 2 and X-ray detector 3 in unison.

The image pickup revolving unit 4 and top board driving unit 5 perform the respective controls upon instructions transmitted from an imaging controller 9 at appropriate times in response to inputs made through a console 8 or the like. The emission control unit 6 performs the controls upon instructions transmitted at appropriate times from a pre-CT controller 10 and a production CT controller 11 (which will be described in detail hereinafter).

In this embodiment, the X-ray detection data outputted from the X-ray detector 3 as the fan beam FB is emitted from the X-ray tube 2 is collected in a data collector (DAS: Data Acquisition System) 12, and is thereafter transmitted to an analog-to-digital converter 13 for digitizing the data. Following the analog-to-digital converter 13 in arrangement are a detection data memory 14 for storing the X-ray detection data, an image reconstruct unit 15 for performing a three-dimensional image reconstructing process based on the X-ray detection data, a CT image memory 16 for temporarily storing CT images made, and a display monitor 17 for displaying the CT images. The X-ray CT apparatus further includes a printer (not shown) for printing the CT images on sheets as X-ray pictures, and a memory (not shown) for storing the CT images in the form of image signals.

The X-ray CT apparatus in this embodiment includes the pre-CT controller 10 and production CT controller 11. The pre-CT controller 10 controls the emission control unit 6 to irradiate the patient M with low doses of fan beam FB (e.g. sets a relatively small X-ray tube current). The production CT controller 11 controls the emission control unit 6 to irradiate the patient M with predetermined doses of fan beam FB (e.g. sets a predetermined X-ray tube current suited to radiography).

The X-ray CT apparatus in this embodiment performs a radiographic process with a contrast medium given to the patient, as follows. Upon receipt of a radiography starting instruction from the console 8, the imaging controller 9 outputs a radiography starting command to execute a pre-CT with low doses. The pre-CT is executed for monitoring purposes to determine the timing of starting a production CT. Upon confirmation by the pre-CT that the contrast medium has fully spread to a region of concern of patient M, the production CT is started to acquire clear CT images for use in diagnosis. Of course, the patient M is exposed to a less quantity of X-ray radiation in the pre-CT than in the production CT. The pre-CT provides all the less clear CT images. However, the pre-CT is executed only to determine a coloring state of the contrast medium, and the indistinctness of the CT images presents no problem.

The X-ray CT apparatus in this embodiment includes a radiographic mode setter (pre-CT setting device) 19 as a characterizing construction thereof. In response to an input made through the console 8, the radiographic mode setter 19 selects one of three radiographic modes for the pre-CT. These modes are a continuous radiographic mode for performing only a continuous radiography (continuous scan), an intermittent radiographic mode for performing only an intermittent radiography (intermittent scan), and a combined intermittent and continuous radiographic mode for performing an intermittent radiography and a continuous radiography in combination.

Figure 4A:
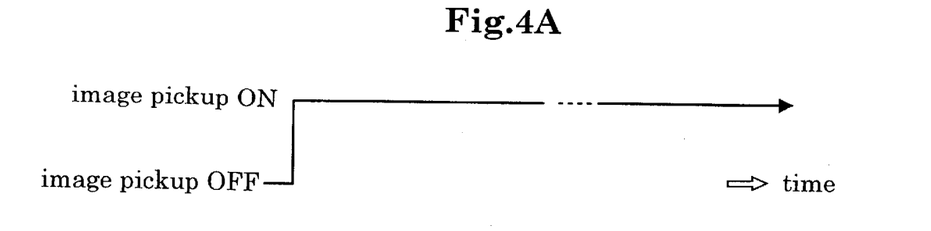
FIG. 4A shows a continuous radiographic mode.
Figure 4B:
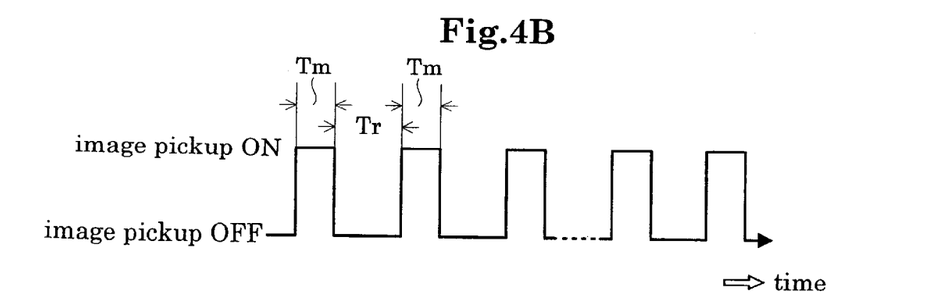
FIG. 4B shows an intermittent radiographic mode.
Figure 4C:
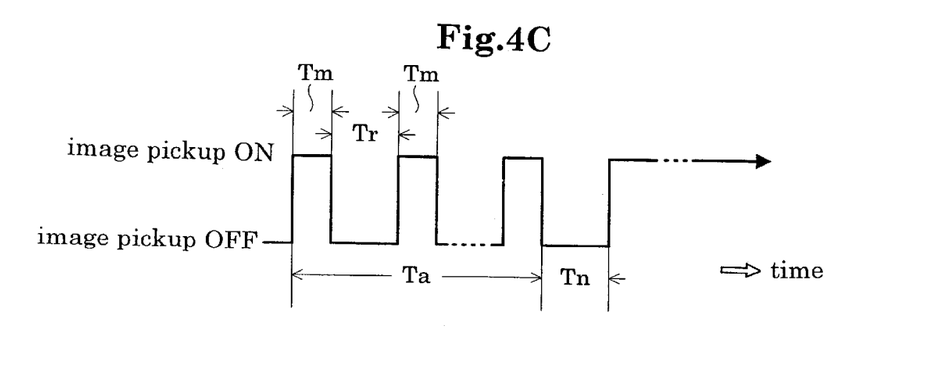
FIG. 4C shows a combined intermittent and continuous radiographic modes.

Specifically, in the continuous radiographic mode, as shown in FIG. 4A, X rays are continuously emitted in low doses to pick up images without a break. This radiographic mode is employed where, for example, it is difficult to predict when the region of concern of the patient M will be stained with a contrast medium. In the intermittent radiographic mode, as shown in FIG. 4B, X rays are intermittently emitted in low doses, with an interval Tr between one image pickup period Tm and another. This intermittent radiographic mode is employed where, for example, the time at which the region of concern is stained with a contrast medium is not very important. In the combined intermittent and continuous radiographic mode, as shown in FIG. 4C, images are continuously picked up after a waiting time Tn following a predetermined period Ta including the image pickup periods Tm and intervals Tr. This combined radiographic mode is selected more frequently than the other two modes, where, for example, the time at which the region of concern is stained with a contrast medium can be predicted with some degree of certainty. Naturally, exposure dose is less for the period of intermittent radiography than for the period of continuous radiography.

The image pickup periods Tm, intervals Tr, predetermined period Ta and waiting time Tn in the respective radiographic modes may be set by operating the console 8. A frequency of image pickup periods Tm may be set in place of the predetermined period Ta.

The radiographic mode setter 19 in the embodiment is operable to set the combined intermittent and continuous radiographic mode in various other ways, besides the form shown in FIG. 4C where an intermittent radiography is followed by a continuous radiography. These variations include, for example, a case of executing a continuous radiography before an intermittent radiography, a case of executing a continuous radiography, an intermittent radiography and a continuous radiography again, and a case of executing an intermittent radiography, a continuous radiography and an intermittent radiography again. Thus, depending on a form selected, it may be necessary to set a different period for continuous radiography, or a different waiting time before switching from continuous radiography to intermittent radiography.

A radiographic mode selected by operating the console 8 is stored in the radiographic mode setter 19. The pre-CT controller 10 refers to the radiographic mode stored in the radiographic mode setter 19, and performs required controls of the emission control unit 6.

The production CT controller 11 performs required controls of the emission control unit 6 in response to radiographic conditions selected by inputs made through the console 8.

The apparatus in this embodiment includes a delay time setter 20 for setting a delay time from a point of time when a pre-CT starting instruction is given to a point of time when a pre-CT is actually executed. A delay time or no delay time, and a duration of a delay time, if any, may be set by inputs made through the console 8. Normally, a delay time lasts about ten seconds, for example.

Figure 5:
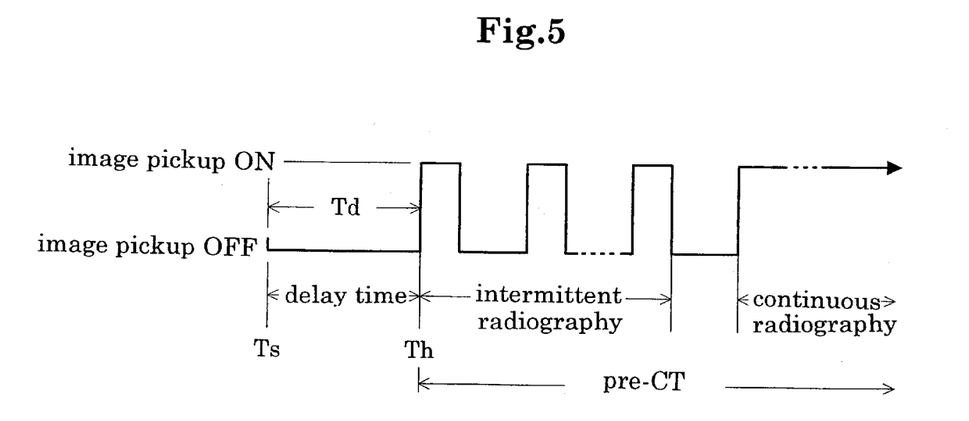
FIG. 5 is a graph showing a radiographic mode of the pre-CT with a delay time.

A delay time may be set to each radiographic mode of the pre-CT. Where a delay time is set to the combined radiographic mode, as shown in FIG. 5, for example, the pre-CT controller 10 starts an intermittent radiography at a point of time Th when delay time Td elapses from a point of time Ts of a radiography starting instruction.

The apparatus in this embodiment further includes a production CT automatic starter 18 for automatically starting a production CT upon detection that a predetermined region of concern in CT images acquired from a pre-CT has a CT value has reached a predetermined reference CT value. The production CT automatic starting unit 18 includes a region of concern setter 18a for setting a predetermined region of concern in the CT images, a reference CT value holder 18b for holding a reference CT value set beforehand, a measured CT value computing unit 18c for computing, as a measured CT value, an average CT value of all pixels in the predetermined region of concern in each CT image, and a CT value comparator 18d for transmitting a detection signal to the two CT controllers 10 and 11 when the measured CT value reaches the reference CT value. The pre-CT controller 10 stops radiography upon receipt of the detection signal, while the production CT controller 11 starts radiography upon receipt of the detection signal.

Figure 6:
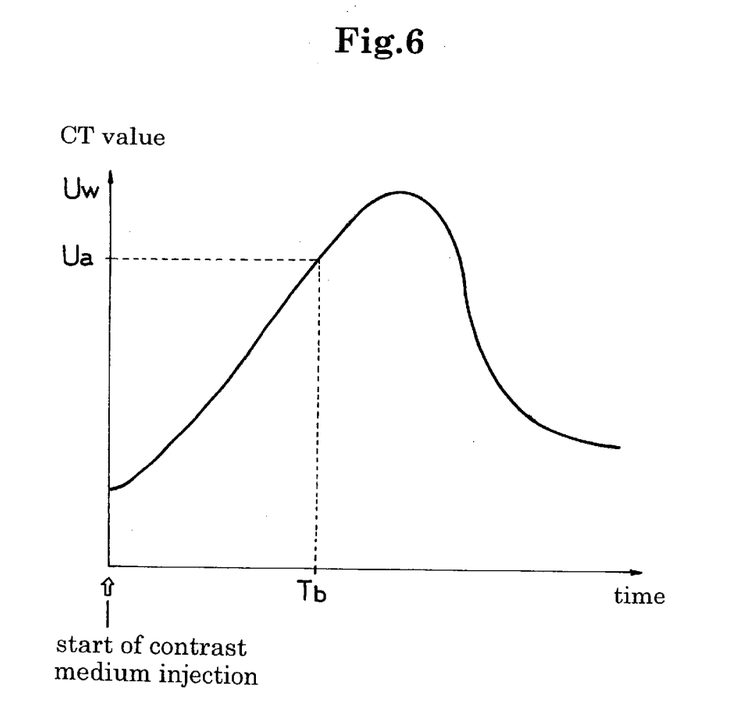
FIG. 6 is a graph showing a relationship between elapsed time from a start of contrast medium injection and CT values measured.

As shown in FIG. 6, measured CT value Uw in the region of concern gradually increases to a peak, and then gradually decreases, with the passage of time from a start of contrast medium injection. On the other hand, the measured CT value Uw is in a corresponding relationship with the coloring state of the contrast medium. Thus, a reference CT value Ua invariable with time, for example, may be determined and set beforehand which corresponds to a coloring state of the contrast medium for starting a production CT. At a point of time Tb when the measured CT value Uw reaches the reference CT value Ua, the pre-CT is stopped and the production CT started.

The reference CT value Ua is set to the reference CT value holder 18b by an input made through the console 8. A region of concern is set to the region of concern setter 18a by the operator inputting the region to the console 8 while observing a CT image acquired, for example, from a test radiography in a preparatory stage and displayed on the screen of display monitor 17.

Figure 7:
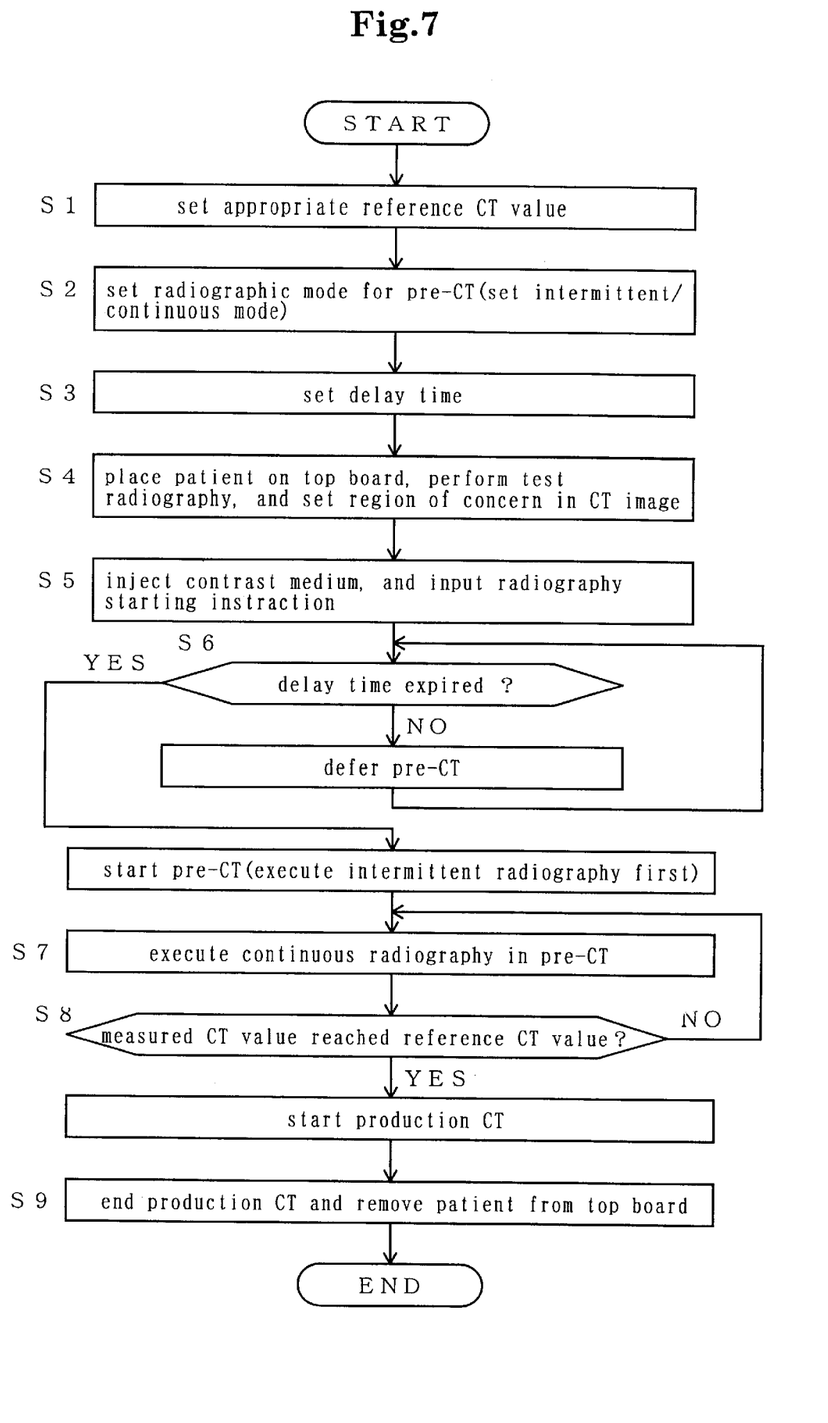
FIG. 7 is a flow chart showing progress of an X-ray CT by the apparatus embodying this invention.

Next, an operation of the X-ray CT apparatus having the construction described above will be described with reference to the drawings. This operation is carried out with a contrast medium injected to pick up sectional images. FIG. 7 is a flow chart showing progress of an X-ray CT by the apparatus in this embodiment.

It is assumed here that the combined intermittent and continuous radiographic mode is selected as the radiographic mode for a pre-CT, and that a delay time is set.

[Step S1] An input is made through the console 8 to set a suitable reference CT value Ua to the reference CT value holder 18b according to the purpose of radiography.

[Step S2] Inputs are made through the console 8 to select the combined intermittent and continuous radiographic mode as the radiographic mode for the pre-CT, and to set the selected mode, along with image pickup periods Tm, intervals Tr, predetermined period Ta and waiting time Tn, to the radiographic mode setter 19.

[Step S3] An input is made through the console 8 to set a suitable delay time Td to the delay time setter 20.

[Step S4] A patient M is placed on the top board 1 and set to a position for image pickup. While observing a CT image acquired from a test CT and displayed on the display monitor 17, the operator carries out an input operation on the console 8 to set a predetermined region of concern in the CT image to the region of concern setter 18a.

[Step S5] The contrast medium is given to the patient M. The operator presses a start button (not shown) on the console 8 to input a radiography start instruction.

[Step S6] Until the delay time Td elapses, the execution of the pre-CT is deferred and an inspection is carried out to check for any leakage of the contrast medium, for example. Upon lapse of the delay time Td, the pre-CT is started. First, an intermittent radiography is executed only for the predetermined period Ta.

[Step S7] Upon lapse of the predetermined period Ta from the start of the pre-CT, a switch is made from the intermittent radiography to the continuous radiography.

[Step S8] The continuous radiography of the pre-CT is continued until the measured CT value Uw reaches the reference CT value Ua. When the measured CT value Uw reaches the reference CT value Ua, a switch is made automatically to a production CT.

[Step S9] After the production CT the patient M is removed from the top board 1 to complete the radiography.

With the X-ray CT apparatus in the embodiment described above, an appropriate pre-CT may be carried out by selecting a radiographic mode suited to the purpose of radiography from among the three different radiographic modes. Consequently, a coloring state of the contrast medium in the region of concern of patient M to be radiographed is accurately determined to determine a proper time for starting a production CT.

The apparatus in the described embodiment, with the delay time setting function, secures the association between a point of time for starting a pre-CT and a point of time for starting a contrast medium injection, and the association between the timing of a switch from intermittent radiography to continuous radiography in the pre-CT and the point of time for starting the contrast medium injection. Thus, a pre-CT may be started, and a switch made from intermittent radiography to continuous radiography, always with appropriate timing. As a result, a time for starting a production CT is determined accurately.

The apparatus in the described embodiment is convenient in that a switch is automatically made from pre-CT to production CT, without requiring an operation by the operator, when the measured CT value reaches the reference CT value.

This invention is not limited to the above embodiment, but may be implemented in modified forms as follows:

(1) In the foregoing embodiment, a switch is made from pre-CT to production CT when the measured CT value of a predetermined region of concern in a CT image reaches the reference CT value. An apparatus may be cited as a modification in which the operator observes a predetermined region of concern in CT images to determine whether the coloring state of the contrast medium is suitable or not, and manually switches from pre-CT to production CT when the coloring state of the contrast medium is found suitable.

(2) In the foregoing embodiment, the combined intermittent and continuous radiographic mode may be executed in varied combinations of intermittent radiography and continuous radiography. An apparatus may be cited as a modification in which only the combination of intermittent radiography and continuous radiography shown in FIG. 2(c) is available as the combined radiographic mode.

Figure 8:
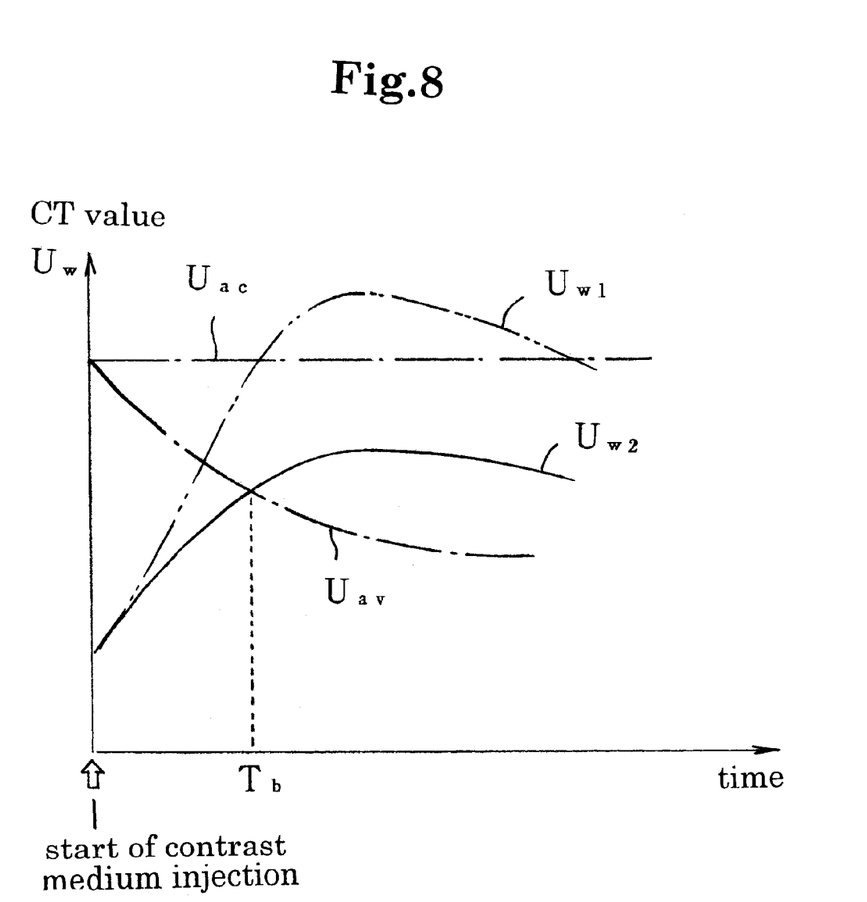
FIG. 8 is a graph showing a reference CT value variable with time.

(3) In the foregoing embodiment, a reference CT value Ua invariable with time is set as shown in FIG. 6. Instead, a reference CT value Ua variable with time may be set. As shown in FIG. 8, for example, the measured CT value Uw of a region of concern, i.e. the coloring state of a contrast medium in the region of concern, is variable from patient to patient. Thus, a measured CT value $Uw_2$ shown in a solid line in FIG. 8 may be lower than an ordinary measured CT value $Uw_1$. In such a case, with a reference CT value Uac invariable with time set to suit the ordinary measured CT value $Uw_1$, the time Tb for switching from pre-CT to production CT could not be detected for a patient showing the low-level measured CT value $Uw_2$. Thus, as shown in FIG. 8, a reference CT value Uav variable (decreasing in this example) with time may be set. By setting the reference CT value Uav variable with time, a switch may be made properly from pre-CT to production CT regardless of the difference with the individual patient. The reference CT value Uav variable with time is not necessarily the one that decreases with time. A reference CT value Uav increasing or decreasing stepwise may be set as appropriate.

The present invention may be embodied in other specific forms without departing from the spirit or essential attributes thereof and, accordingly, reference should be made to the appended claims, rather than to the foregoing specification, as indicating the scope of the invention.

What is claimed is:

1. An X-ray CT apparatus for performing a pre-CT which is a form of computerized tomography carried out with low doses beforehand in order to determine timing of starting a production CT which is a form of computerized tomography for acquiring images for use in diagnosis, said apparatus comprising:

X-ray emitting means for emitting X rays toward a patient;

X-ray detecting means for detecting X rays transmitted through the patient;

revolving means for revolving said X-ray emitting means and said X-ray detecting means about the patient;

image reconstructing means for reconstructing sectional images of the patient based on X-ray detection data received from said X-ray detecting means;

pre-CT control means for controlling said X-ray emitting means according to a radiographic mode of said pre-CT;

production CT control means for controlling said X-ray emitting means according to radiographic conditions of said production CT; and pre-CT radiographic mode setting means for selecting and setting, as said radiographic mode of said pre-CT, one of three radiographic modes, i.e. a continuous radiographic mode for performing only a continuous radiography by continuously emitting X rays in low doses, an intermittent radiographic mode for performing only an intermittent radiography by intermittently emitting X rays in low doses, and a combined intermittent and continuous radiographic mode for performing said intermittent radiography and said continuous radiography in combination.

2. An X-ray CT apparatus as defined in claim 1, wherein said pre-CT radiographic mode setting means is constructed for setting at least image pickup periods which are X-ray emitting periods in said intermittent radiography, and intervals between said image pickup periods.

3. An X-ray CT apparatus as defined in claim 1, further comprising delay time setting means for setting a delay time lasting from a point of time when a pre-CT starting instruction is given to a point of time for starting said pre-CT.

4. An X-ray CT apparatus as defined in claim 1, further comprising production CT automatic starting means for automatically starting said production CT upon detection of a measured CT value of a predetermined region of concern in sectional images acquired from said pre-CT having reached a predetermined reference CT value.

5. An X-ray CT apparatus as defined in claim 4, wherein said measured CT value is an average CT value of all pixels in said region of concern.

6. An X-ray CT apparatus as defined in claim 5, further comprising console means for designating and inputting said region of concern on a display monitor screen displaying said sectional images of the patient.

7. An X-ray CT apparatus as defined in claim 4, wherein said reference CT value is invariable with time.

8. An X-ray CT apparatus as defined in claim 4, wherein said reference CT value is variable with time.

* * * * *